United States Patent

Rogers et al.

[11] Patent Number: 6,074,366
[45] Date of Patent: Jun. 13, 2000

[54] MEDICATION DELIVERY APPARATUS

[75] Inventors: Bobby E. Rogers, Del Mar; Marc S. Lieberman, Poway; Marc C. Doyle, San Diego, all of Calif.

[73] Assignee: Tandem Medical Inc., San Diego, Calif.

[21] Appl. No.: 09/008,111

[22] Filed: Jan. 16, 1998

[51] Int. Cl.[7] ................................................. A61M 1/00
[52] U.S. Cl. .............................. 604/151; 604/65; 604/81; 604/410
[58] Field of Search ................................. 604/151, 131, 604/80, 82, 83, 403, 404, 407, 408, 409, 410, 415, 65.67; 141/100, 114, 9, 325, 326

[56] References Cited

U.S. PATENT DOCUMENTS

| | | | |
|---|---|---|---|
| 2,124,907 | 7/1938 | Bunting | 221/60 |
| 2,168,080 | 8/1939 | Allen | 221/60 |
| 2,461,891 | 2/1949 | Giles | 222/101 |
| 2,742,189 | 4/1956 | Morrison | 222/100 |
| 3,198,385 | 8/1965 | Maxwell | 222/41 |
| 3,469,578 | 9/1969 | Bierman | 128/214 |
| 3,543,966 | 12/1970 | Ryan et al. | 222/94 |
| 3,640,277 | 2/1972 | Adelberg | 128/214 F |
| 3,647,117 | 3/1972 | Hargest | 222/100 |
| 3,670,926 | 6/1972 | Hill | 222/47 |
| 4,019,655 | 4/1977 | Moeller | 222/96 |
| 4,258,864 | 3/1981 | Karamanolis et al. | 222/96 |
| 4,337,769 | 7/1982 | Olson | 128/214 |
| 4,364,474 | 12/1982 | Hollander, Jr. | 206/219 |
| 4,399,103 | 8/1983 | Ferrara | 422/100 |
| 4,504,267 | 3/1985 | Parmelee et al. | 604/134 |
| 4,507,114 | 3/1985 | Bohman et al. | 604/410 X |
| 4,512,764 | 4/1985 | Wunsch | 604/80 |
| 4,522,622 | 6/1985 | Peery et al. | 604/191 |
| 4,525,164 | 6/1985 | Loeb | 604/131 |
| 4,557,728 | 12/1985 | Sealfon et al. | 604/134 |
| 4,559,036 | 12/1985 | Wunsch | 604/81 |
| 4,576,314 | 3/1986 | Elias et al. | 222/97 |
| 4,576,603 | 3/1986 | Moss | 604/410 |
| 4,626,243 | 12/1986 | Singh et al. | 604/141 |
| 4,666,430 | 5/1987 | Brown et al. | 604/141 |
| 4,667,854 | 5/1987 | McDermott et al. | 222/101 |
| 4,730,058 | 3/1988 | Doan | 604/155 |
| 4,741,736 | 5/1988 | Brown | 604/134 |
| 4,753,371 | 6/1988 | Michielin et al. | 222/144.5 |
| 4,765,512 | 8/1988 | Bull, Jr. | 222/100 |
| 4,772,263 | 9/1988 | Dorman et al. | 604/132 |
| 4,784,157 | 11/1988 | Halls et al. | 128/762 |
| 4,795,441 | 1/1989 | Bhatt | 604/124 |
| 4,823,833 | 4/1989 | Hogan et al. | 137/567 |
| 4,830,510 | 5/1989 | Bellhouse | 366/219 |
| 4,842,576 | 6/1989 | Lysaght et al. | 604/6 |

(List continued on next page.)

FOREIGN PATENT DOCUMENTS

| | | | |
|---|---|---|---|
| 0 145 825 | 6/1985 | European Pat. Off. | A61J 1/00 |
| 0 790 051 A2 | 8/1997 | European Pat. Off. | A61J 1/10 |

OTHER PUBLICATIONS

I–Flow VIvUS 50 and VIVUS 100, Data Sheets, 5 pages, Jun. 1993.

*Primary Examiner*—John D. Yasko
*Attorney, Agent, or Firm*—Gray Cary Ware & Freidenrich LLP; Stephen E. Reiter; Ramsey R. Stewart

[57] ABSTRACT

It is a primary object of the present invention to provide an automated system based on an integral fluid bag for administering a variety of intravenous drug regimens and reducing the vagaries of existing manual systems. The fluid has multiple chambers configured to implement a prescribed intravenous medical therapy. Each chamber's geometry (size, shape), sequence and position, alone and in combination with the other chambers, matches the prescribed intravenous therapy or drug regimen. The bag's configuration assures that the intravenous therapy is administered in accordance with the prescribed drug regimen, thus automating the previous manual method. A choice of fluid bag configurations may be stocked so that a prescription for well known and widely accepted drug regimens may be filled by merely selecting a bag with the appropriate chamber configuration and filling it with the prescribed medications.

26 Claims, 13 Drawing Sheets

U.S. PATENT DOCUMENTS

| | | | |
|---|---|---|---|
| 4,846,637 | 7/1989 | Alderson et al. | 417/479 |
| 4,850,725 | 7/1989 | Walker et al. | 400/236.2 |
| 4,850,971 | 7/1989 | Colvin | 604/134 |
| 4,857,055 | 8/1989 | Wang | 604/133 |
| 4,898,583 | 2/1990 | Borsanyi et al. | 604/153 |
| 4,915,688 | 4/1990 | Bischof et al. | 604/83 |
| 4,957,436 | 9/1990 | Ryder | 433/88 |
| 4,966,579 | 10/1990 | Polaschegg | 604/65 |
| 4,997,083 | 3/1991 | Loretti et al. | 206/219 |
| 5,048,725 | 9/1991 | Peterson | 222/100 |
| 5,080,652 | 1/1992 | Sancoff et al. | 604/132 |
| 5,105,983 | 4/1992 | Sancoff et al. | 222/103 |
| 5,118,011 | 6/1992 | Kopp | 222/102 |
| 5,176,634 | 1/1993 | Smith et al. | 604/410 X |
| 5,199,604 | 4/1993 | Palmer et al. | 222/25 |
| 5,205,820 | 4/1993 | Kriesel | 604/85 |
| 5,207,645 | 5/1993 | Ross et al. | 604/141 |
| 5,211,626 | 5/1993 | Frank et al. | 604/65 |
| 5,219,331 | 6/1993 | Vanderveen | 604/81 |
| 5,308,334 | 5/1994 | Sancoff | 604/131 |
| 5,308,335 | 5/1994 | Ross et al. | 604/141 |
| 5,318,515 | 6/1994 | Wilk | 604/30 |
| 5,330,431 | 7/1994 | Herskowitz | 604/153 |
| 5,342,313 | 8/1994 | Campbell et al. | 604/153 |
| 5,368,570 | 11/1994 | Thompson et al. | 604/131 |
| 5,377,871 | 1/1995 | Banks et al. | 222/41 |
| 5,394,907 | 3/1995 | Hjertman et al. | 141/1 |
| 5,411,490 | 5/1995 | Tennican et al. | 604/236 |
| 5,431,496 | 7/1995 | Balteau et al. | 604/410 X |
| 5,433,704 | 7/1995 | Ross et al. | 604/67 |
| 5,492,533 | 2/1996 | Kriesel | 604/132 |
| 5,505,708 | 4/1996 | Atkinson | 604/140 |
| 5,509,898 | 4/1996 | Isono et al. | 604/87 |
| 5,560,518 | 10/1996 | Catterall et al. | 222/99 |
| 5,578,001 | 11/1996 | Shah | 604/31 |
| 5,578,005 | 11/1996 | Sancoff et al. | 604/82 |
| 5,628,429 | 5/1997 | Usen et al. | 222/1 |
| 5,692,645 | 12/1997 | Ryu | 222/101 |
| 5,775,540 | 7/1998 | Greenberg | 222/102 |
| 5,853,388 | 12/1998 | Semel | 604/82 |

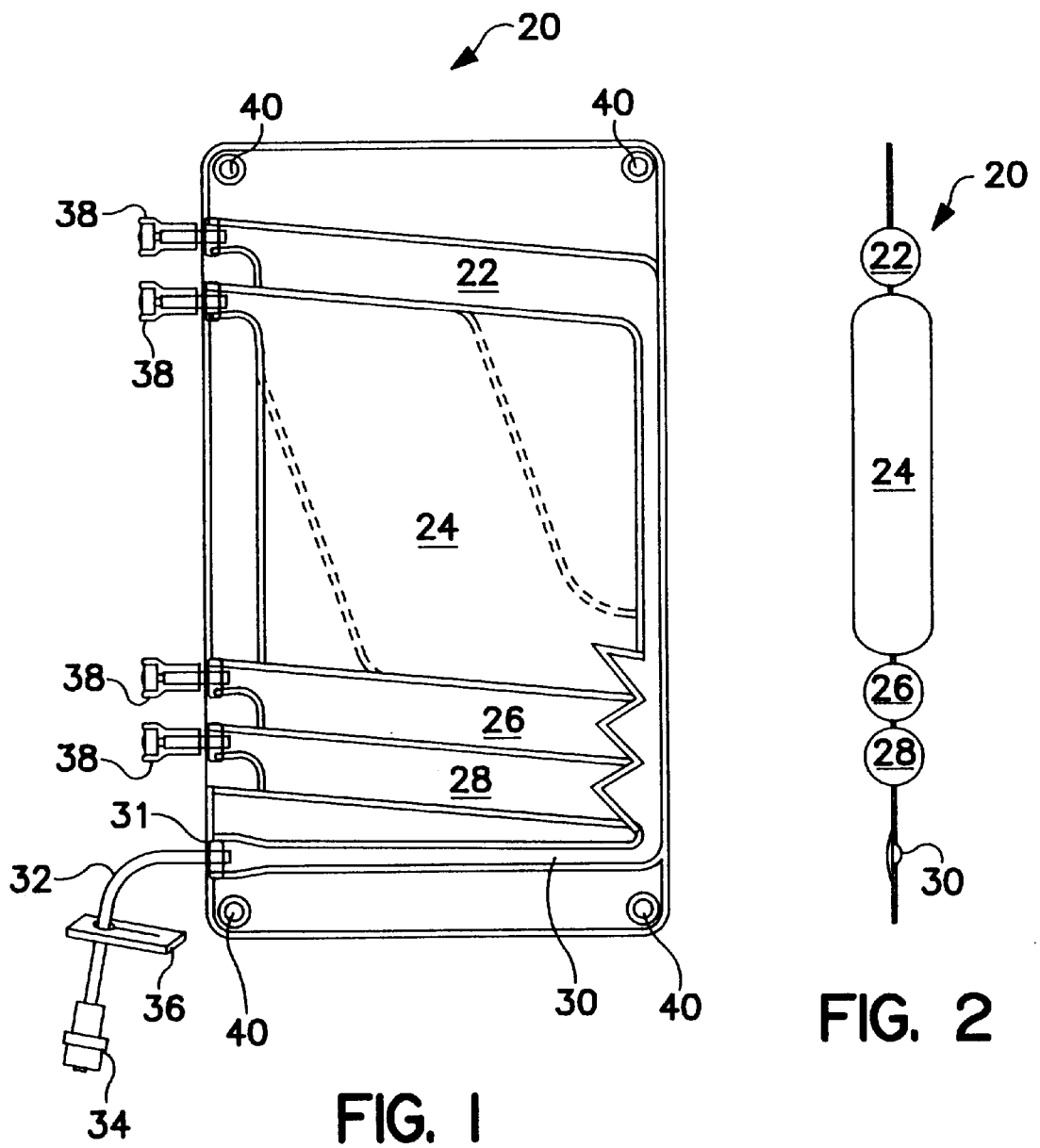

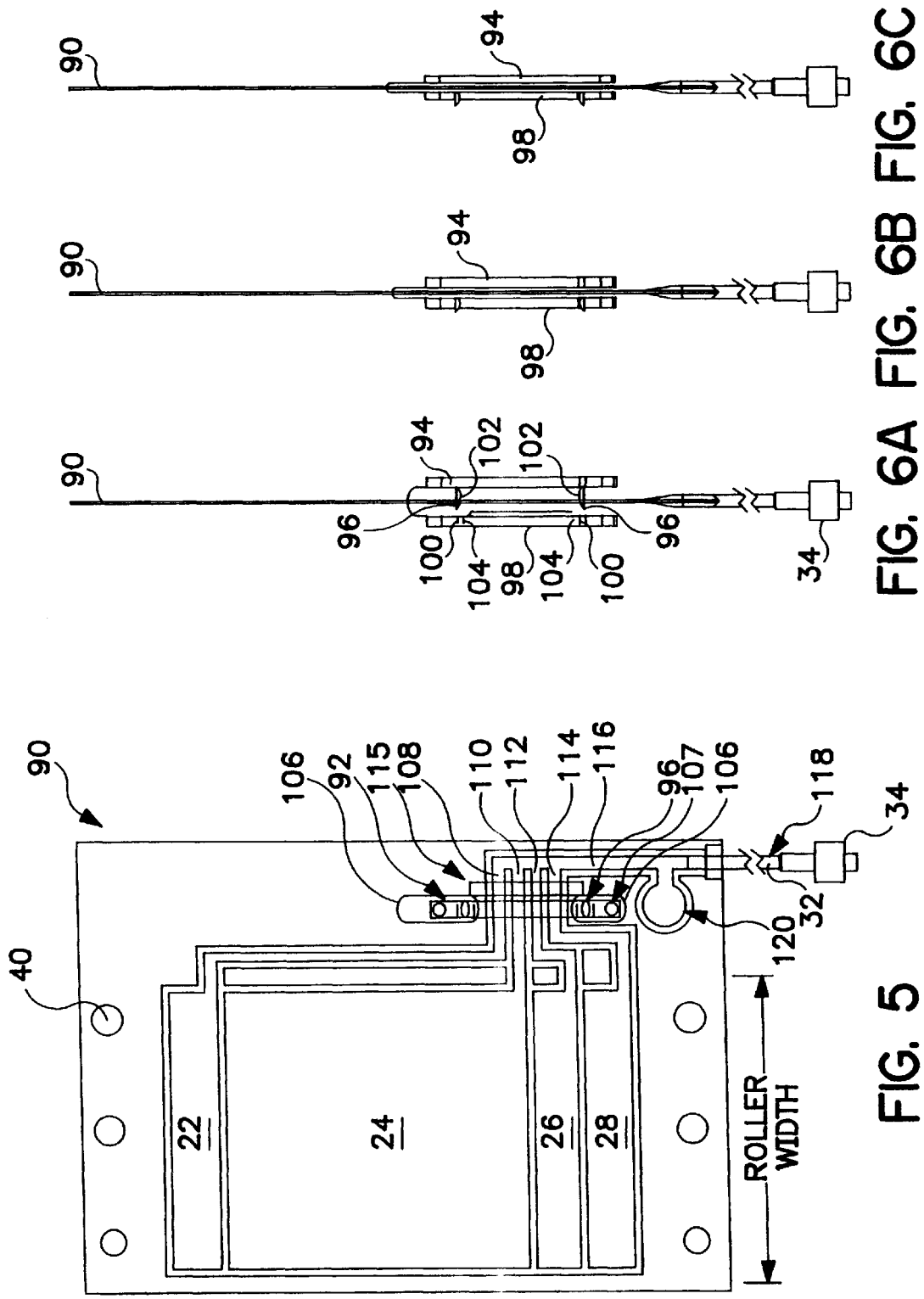

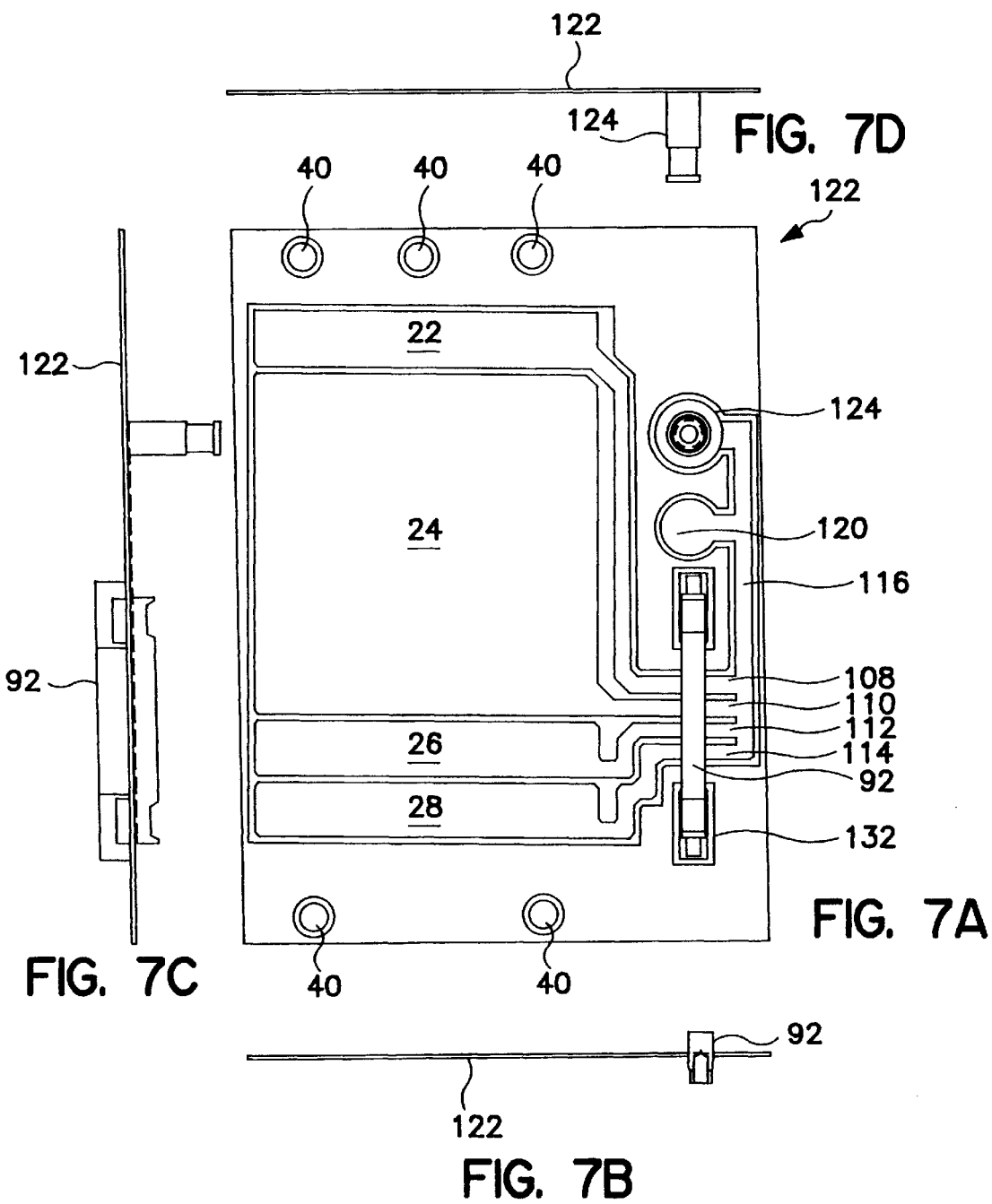

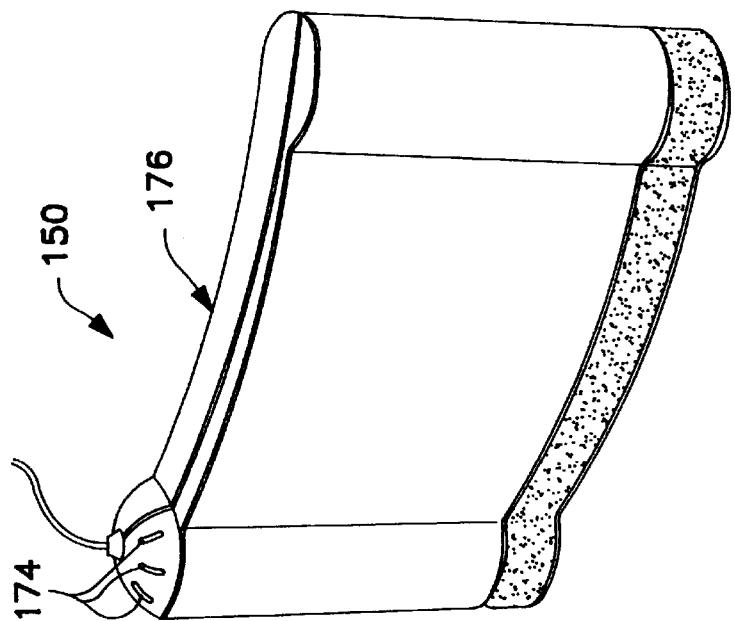
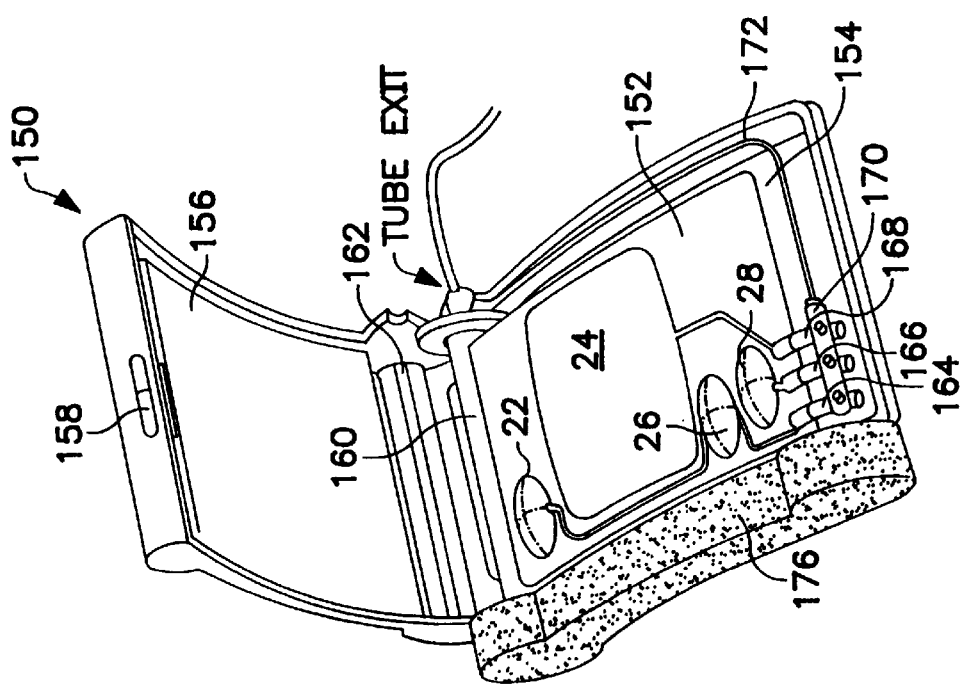
FIG. 9A
FIG. 9B

MEDICATION DELIVERY APPARATUS

FIELD OF THE INVENTION

The invention relates generally to apparatus and methods for the intravenous infusion of medication and, more particularly, to the automatic administration of intermittent medications in accordance with a predetermined medical therapy. A multichamber fluid bag is manufactured with a particular chamber size and geometry for implementing a prescribed infusion therapy. Because the infusion therapy is implemented by the bag's chamber configuration, the administration of a complex medical infusion therapy is simplified.

BACKGROUND OF THE INVENTION

It is now common for intravenous medications such as antibiotics, antivirals, antiemetics, chemotherapy and biotechnology drugs to be administered intermittently with a frequency as often as multiple times per day. Depending on the frequency of administration, the patient is either repeatedly connected to and disconnected from an intravenous (I.V.) line or is continuously connected to an I.V. line between administrations. In either case, the intermittent medications are generally administered by trained personnel using predefined procedures that often include a series of manual steps and a large number of disposable supplies. Each manual step in these procedures increases the risks associated with multiple manipulations and entry of I.V. sites.

The predefined procedures attempt to ensure the proper administration and the proper dosing of medication, while preventing incompatibilities between different drugs and preventing I.V. lines from clotting off between doses. Unfortunately, because of the manual steps included in these procedures, they have not been entirely successful in guaranteeing that medications are administered in the correct sequence, at the correct infusion rates, and in the correct volumes. Further, if the appropriate procedural steps are not performed within the required time frames, clots may form in the I.V. lines. Also, the manual steps included in these administration procedures are the principle source of infection and other complications that may arise during intermittent infusion therapy. Such problems and complications result in a longer hospital stay for the affected patient. Recent trends which have the patient trained to administer their own medications at home only exacerbate the problems and risks associated with intermittent infusion therapy. Further, elaborate or complicated infusion procedures are more likely to give rise to patient non-compliance by an untrained and less sophisticated home infusion patient.

Accordingly, there exists a definite need for an apparatus and related method for simplifying the administration of intermittent medical infusion therapy. The present invention satisfies these needs.

SUMMARY OF THE INVENTION

The present invention is embodied in a fluid delivery apparatus for the automated sequential or concurrent infusion of a plurality of pharmacological agents. The apparatus includes a plurality of chambers each configured with a respective geometry. Each chamber configuration controls the volume of each pharmacological agent administered, the rate at which each pharmacological agent is administered, and the regimen with which said pharmacological agent is administered.

In more detailed features of the invention, the fluid delivery apparatus may further include a common passageway and a plurality of chamber passageways. Each chamber passageway is coupled between the common passageway and a respective chamber. The fluid delivery apparatus may also include a high pressure clip having at least first and second positions, wherein, in the first position, the clip closes the plurality of chamber passageways and, in the second position, the clip permits fluid flow through the plurality of chamber passageways. The apparatus may also include a pressure sensing dome in fluid communication with the common passageway. Further, a frangible rupture seal may be situated between at least one chamber and the corresponding chamber passageway. Also, at least one chamber includes a sealable fill port and a sealable vent port.

In other more detailed features of the invention, the fluid delivery apparatus may further include an infusion pump with a spring driven roller for sequentially compressing the plurality of chambers. The pump may include a hinged door having a release tab. Alternatively, infusion pump may be actuated by an electrically driven motor for applying pressure to the chambers. The infusion pump may further include a display having status indicator lights, dose buttons, control buttons, a keypad, and a clock for controlling and indicating the status of an agent administration.

In another alternative, the infusion pump may have one or more inflatable bladders for applying pressure to the chambers. Further, a flexible bladder pad may be coupled to a series of bladders for transferring pressure from the series of bladders to the chambers and locally distributing the force applied by any one of the series of bladders.

In an alternative embodiment, the invention is embodied in a fluid bag that is to be filled with pharmacological fluids associated with a desired medical infusion therapy for treatment of a patient. The bag has a plurality of chambers for containing the pharmacological fluids. Each chamber is sized and configured to implement the desired medical therapy when the fluids are automatically infused into the patient. The bag may be a unitary bag forming cartridge and the plurality of chambers lie substantially in a plane.

In yet another embodiment, the invention is embodied in an automated fluid delivery apparatus for sequentially or concurrently infusing medications. The apparatus includes a fluid bag which is constructed from medical grade plastic sheets that are bonded together in a manner to define a plurality of separate chambers. The chambers lie in a plane and are configured with a respective geometry, position, and sequence for controlling the rate, volume and time of medication administration.

The present invention provides an automated system for administering a variety of known drug regimens, thus eliminating the problems associated with the manual infusion system. Because the system uses an intravenous bag having multiple chambers with particular configurations, the contents of the bag can only be administered in accordance with the prescribed manner.

BRIEF DESCRIPTION OF THE DRAWINGS

FIG. 1 is a plan view of a fluid bag, according to the invention, having chambers with geometries configured for implementing a medical infusion therapy.

FIG. 2 is a side elevation view of the fluid bag of FIG. 1.

FIG. 5 is a plan view of a fluid bag having a high pressure clip and a low pressure clamp pad for controlling fluid flow from the chambers.

FIGS. 6A–6C are elevation side views of the fluid bag of FIG. 5, showing the exit port clip in its pre-installation, open, and closed positions, respectively.

FIGS. 7A–7D are isometric views of a fluid bag, according to the invention, having an integral fluid port, pressure monitoring pad, and port clip.

FIGS. 9A and 9B are perspective views of an infusion pump, according to the invention, having a chamber configured to receive the fluid bag of FIG. 1 and opposing rollers for infusing the fluids contained in the respective chambers in a prescribed sequence and rate defined by the bag chamber geometries and roller speed.

DETAILED DESCRIPTION OF THE INVENTION

Figure 3:
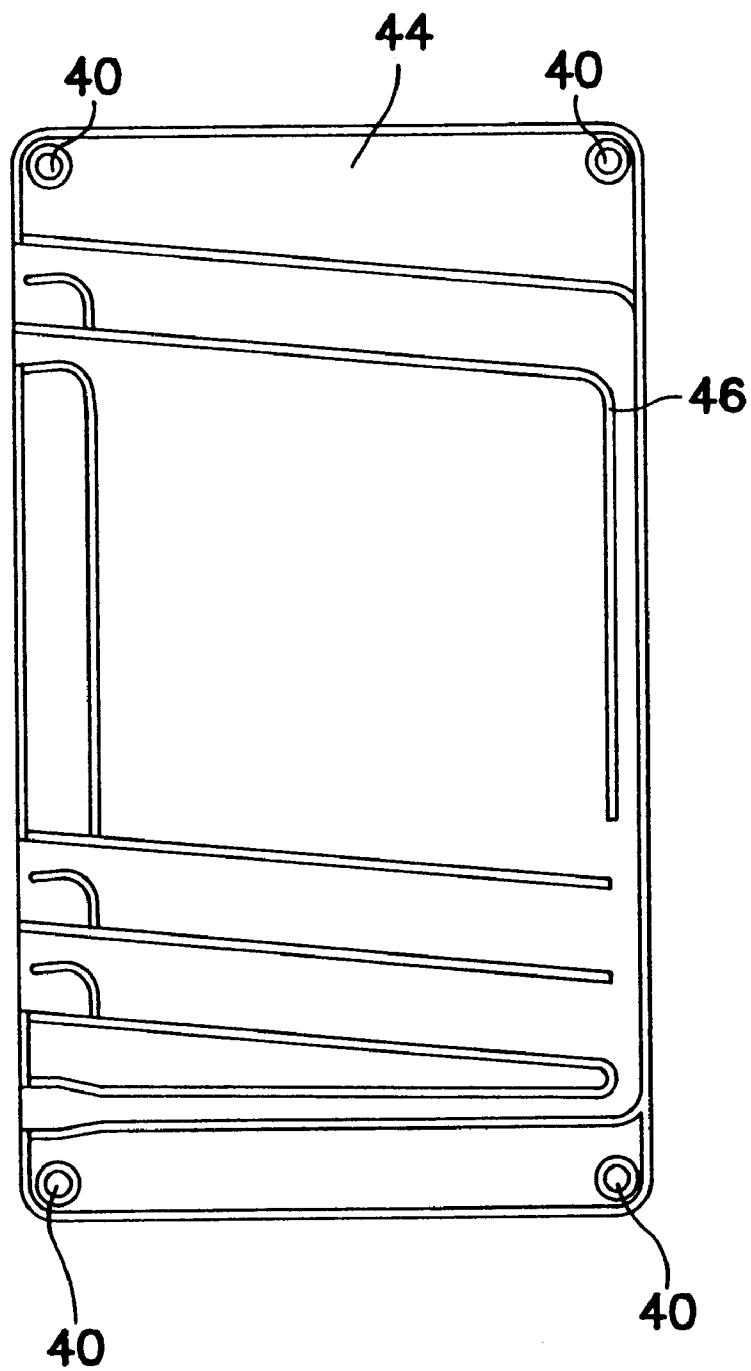
FIG. 3 is a plan view showing a cut and weld pattern for the fluid bag of FIG. 1.

The present invention is embodied in apparatus and related methods for automatically implementing intermittent intravenous medical therapy using a fluid bag having a configuration that largely defines the sequence and flow rate of the infusion of medications into a patient. The invention is advantageous in simplifying the administration of intermittent intravenous medical infusion therapy. A patient (or caregiver), with relatively little medical training, would receive a fluid bag having chambers configured with predetermined geometries and prefilled with prescribed medications and would self-administer the therapy using an infusion pump. Because the therapy is defined by the bag's configuration, the patient, nurse or caregiver would not need to program the infusion pump or perform manual manipulations during the infusion procedure thus substantially reducing the patient's risks due to improper administration.

Referring to FIGS. 1 and 2, the invention is embodied in a multiple chamber fluid bag 20 or cartridge having a plurality of fluid chambers 22, 24, 26 and 28. The bag is a laminate of two flexible plastic sheets attached together to form four separate and distinct chambers and corresponding passageways (not shown) from each chamber to a common passageway 30 and an exit port 31. The unitary bag is relatively flat with the chambers generally lying in a common plane. When chambers are filled with fluid, they expand to have a cylindrical or a "pillow-like" shape. An infusion tube 32 is coupled to the exit port. A connector 34 is coupled to the tube for connection to standard I.V. couplers. A clip 36 is provided on the tube to stop fluid flow through the tube if needed. Although four chambers are shown in FIG. 1, as will be discussed in more detail below, the fluid bag may be configured with any of a wide variety of chamber numbers, positions, sequences, and geometries. Each chamber may also include one or more fill ports 38 for filling the chambers. The bag may also include alignment holes 40 (or other alignment vehicles) for positioning the bag within an infusion pump having corresponding alignment pegs (not shown).

The chambers 22, 24, 26 and 28 may be emptied by applying pressure to the bag 20. As disclosed in U.S. patent application Ser. No. 08/538,158, filed Oct. 2, 1995, the pressure may be applied by a roller traveling from the top of the bag toward its bottom at a steady rate. The disclosure of U.S. patent application Ser. No. 08/538,158 is hereby incorporated by reference. Other apparatus and methods for applying pressure to the chambers are discussed in more detail below.

The chambers of the fluid bag 20 of FIGS. 1 and 2 are suitably configured to implement a SASH infusion therapy. SASH is an acronym for Saline-Antibiotic-Saline-Heparin. The first chamber 22 is typically filled with about 5 ml. of saline solution. The second chamber 24 is typically filled with about 100 ml. of liquid antibiotic. The third and fourth chambers are each typically filled with about 5 ml. of saline solution and heparized solution, respectively.

With reference now to FIG. 3, the bag 20 can be from two flexible sheets of plastic film 44 by welding the sheets together along weld lines 46. The welds may be ultrasonic or heat welds or the like. The weld lines define each chamber's geometry and size thus its volume. The geometry and volume of each chamber defines the sequence and rate at which the corresponding prescribed medication is infused into the patient. The four alignment holes 40 may be cut before or after the sheets are welded. The plastic film may be formed of any medically acceptable plastic polyvinyl chloride (PVC), polyolefin or other suitable material.

The rate at which the medications exit the chambers may be additionally defined by restrictive openings at the exit of each chamber, by a restrictive orifice in the common passageway 30, or by a valve in the infusion tube 32. Exit port openings for controlling the flow rate from the chambers is disclosed in U.S. patent application Ser. No. 08/538,158.

Figure 4A:
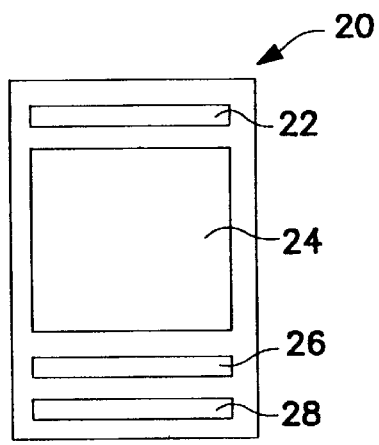
FIGS. 4A–4F are schematic diagrams showing various chamber configurations, according to the invention, for the fluid bag of FIG. 1, each diagram showing a specific chamber configuration with chamber geometries configured for implementing a prescribed medical infusion therapy.
Figure 4B:
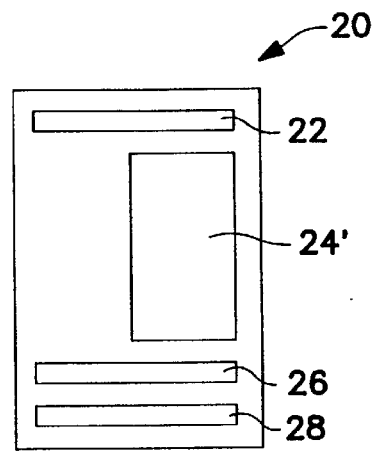
Figure 4C:
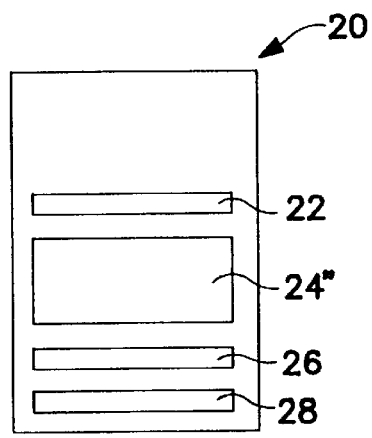

Differing infusion therapies for a wide variety drug regimens may be implemented by the chamber configurations as shown, for example, in FIGS. 4A–4F. For example, as shown, in FIG. 4A the infusion bag 20 is configured with four separate fluid chambers 22, 24, 26 and 28 suitable for implementing a SASH drug regimen. The intravenous antibiotic is contained in the second chamber 24. The volume and shape of the second chamber may be prescribed to affect the volume and the administration rate of the antibiotic as shown in FIGS. 4A–4C. In FIG. 4A, the antibiotic chamber 24 has a square shape and a volume of about 100 ml. In FIG. 4B, the antibiotic chamber 24 has an elongated rectangular shape and a volume of about 50 ml. The antibiotic chamber 24 shown in FIG. 4C, also has a volume of 50 ml, but has a wide shortened rectangular shape. Accordingly, using a constant speed roller that compresses the chambers from top to bottom, the drug prescribed by the bag in FIG. 4B is infused at a slower rate than the drug prescribed by the bag in FIG. 4C. The chamber, of course, is not required to have a rectangular shape and, thus, it may have any shape (e.g., circular, triangular, diamond, etc.) which is beneficial for administering a prescribed infusion therapy.

Figure 4D:
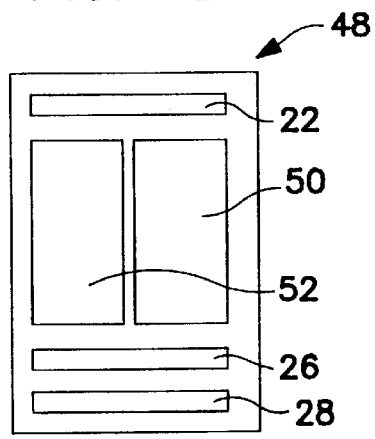

Further, drugs that are incompatible for pre-mixing may be stored in separate chambers until they are simultaneously infused into the patient. As shown in FIG. 4D, simultaneous infusion of separate drugs may be readily accomplished by configuring the bag 48 to have two side-by-side chambers 50 and 52. The first chamber 50 is filled with a first drug and the second chamber 52 is filled with a second drug. Accordingly, as the roller travels down the bag, it simultaneously compresses the two side-by-side drug chambers so that the two drugs are simultaneously infused into the patient thus simplifying the infusion of the two incompatible drugs without pre-mixing.

Figure 4F:
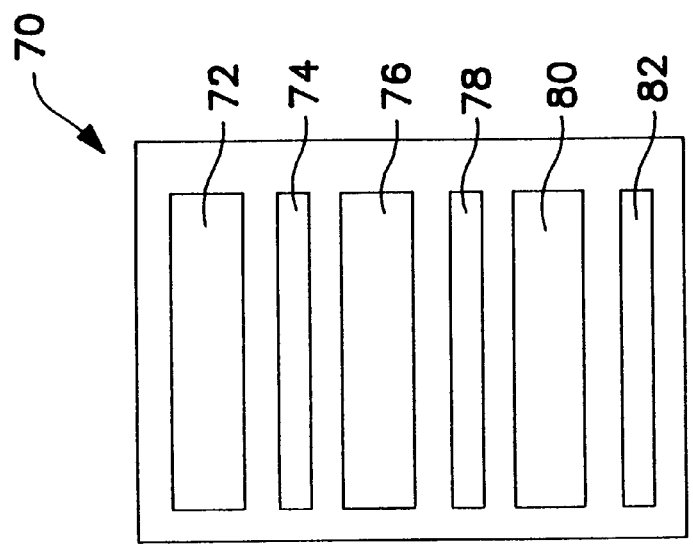
Figure 4E:
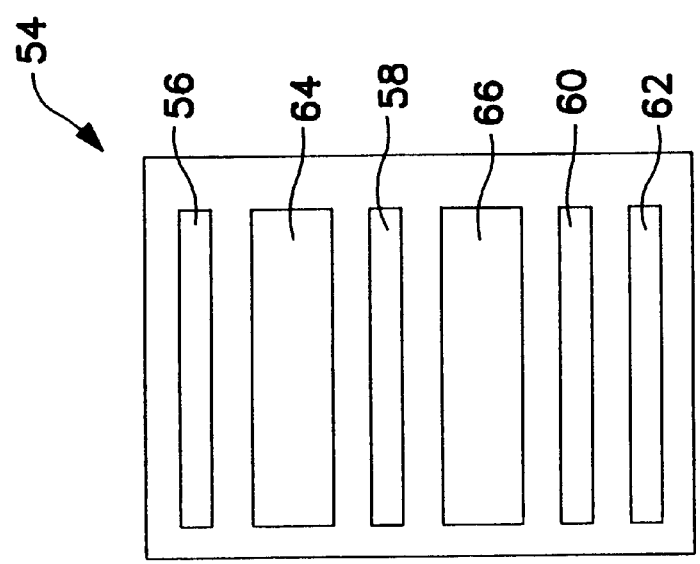

As shown in FIG. 4E, the infusion therapies that may be addressed by configuring the bag's geometry are not limited to the SASH procedure. The bag in FIG. 4E is configured with six separate chambers. The first, third and fifth chambers 56, 58 and 60 can be filled with a saline solution and the sixth chamber 62 can be filled with Heparin. The second and fourth chambers 64 and 66, however, can be filled with first and second drugs, respectively. Of course, this bag may be used to administer intermittent infusions of a single drug by filling the second and fourth chambers with the same drug.

Similarly, as shown in FIG. 4F, multiple doses of a drug may be intermittently administered at prescribed time intervals by a bag 70 having its chambers configured in accordance with the dosage regimen. Thus, the first chamber 72 can be filled with a first prescribed drug dosage, the second chamber 74 can be filled with a saline solution, the third chamber 76 can be filled with a second prescribed drug dosage, the fourth chamber 78 can be filled with a saline solution, the fifth chamber 80 can be filled with a third described drug dosage, and finally, the sixth chamber 82 can be filled with a final saline solution.

Intermittent medications are prescribed using widely accepted medical infusion therapies that are fairly standard for adult patients with similar diagnoses. These standard medical therapies often call for multiple administrations of an infusion regimen each day and rarely change after they are prescribed. Thus a prescription for an infusion regimen is similar to a prescription for an oral antibiotic in that the drug is taken a predetermined number of times per day for a predetermined time period. Accordingly, an infusion patient generally receives a prescription for a particular medical infusion therapy that remains the same for several days. In accordance with the invention, the infusion prescription is filled by a pharmacist having a supply of infusion bags 20 having chambers with differing configurations. The pharmacist would provide the patient with the prescribed number of prefilled bags with the prescribed medication dosages.

The following list is illustrative of the types of drug regimens that may be implemented in a bag in accordance with the invention. Possible drug regimens and possible chamber configurations are not limited to those listed below or shown in the drawings.

PARTIAL LIST OF EXAMPLE DRUG REGIMENS

Antibiotics 1)
5 ml of 0.9% Saline—given quickly or over a few minutes;
1 gram (g) of Cefazolin in 50 ml of 5% Dextrose in Water—given over 60 minutes; and
5 ml of 0.9% Saline—given quickly or over a few minutes.

2)
3 ml of 0.9% Saline—given quickly or over a few minutes;
1 g of Cefazolin in 20 ml of Dextrose (D5W)—given over 30 minutes;
3 ml of 0.9% Saline—given quickly or over a few minute;
1 g of Ceftazidime in 20 ml of Dextrose (D5W)—given over 30 minutes;
3 ml of 0.9% Saline—given quickly or over a few minutes; and
5 ml of 1000 units/mL of Heparized Saline—given quickly or over a few minutes.

3)
5 ml of 0.9% Saline—given quickly or over a few minutes;
80 mg of Gentamicin in 50 ml of 0.9% Saline—given over 60 minutes;
5 ml of 0.9% Saline—given quickly or over a few minutes;
500 mg of Ampicillin in 100 ml of 0.9% Saline—given over 60 minutes;
5 mls of 0.9% Saline—given quickly or over a few minutes; and
5 ml of 100 units/ml of Heparized Saline—given quickly or over a few minutes.

4)
10 ml of 0.9% Saline—given quickly or over a few minutes;
1 g of Vancomycin in 250 ml of 0.9% Saline—given over 90 minutes; and
10 ml of 0.9% Saline—given quickly or over a few minutes.

5)
3 ml of 0.9% Saline—given quickly or over a few minutes;
1 g of Cefazolin in 20 ml of Dextrose (D5W)—given over 30 minutes;
80 mg of Gentamicin in 50 ml of 0.9% Saline—given over 60 minutes;
1 g of Ceptazidime in 100 ml of 0.9% Saline—given over 60 minutes; and
5 ml of 0.9% Saline—given quickly or over a few minutes.

6)
500 mg of Cafazolin in 20 ml of Dextrose (D5W)—given over 30 minutes;
500 mg of Ceptazidime in 20 ml of 0.9% Saline—given over 60 minutes; and
50 mg of Tobramycin in 50 ml of 0.9% Saline—given over 60 minutes.

Anti-Emetic (Nausea) Therapy and Chemotherapy 1)
100 ml of 0.9% Saline given over 30 minutes;
Kytril in 20 ml of 0.9% Saline given over five minutes; and
Cisplatin in 100 ml of 0.9% Saline given over 30 minutes.

Chemotherapy 1)
5 ml of 0.9% Saline—given quickly or over a few minutes;
25 ml of Cyclophosphamide—given over 30 minutes;
25 ml of Doxirubicin—given over 5 minutes;
25 ml of 5-FU—given over 10 minutes; and
5 ml of 0.9% Saline—given quickly or over a few minutes.

2)
10 ml of 0.9% Saline—given quickly or over a few minutes;
10 ml of Vincristine—given over five minutes; and
10 ml of 0.9% Saline—given quickly or over a few minutes.

3)
5 ml of 0.9% Saline—given quickly or over a few minutes;
10 ml of 5-FU—given over 10 minutes;
5 ml of 0.9% Saline—given quickly or over a few minutes; and
5 ml of 100 units/mL of Heparized Saline—given quickly or over a few minutes.

Other (Biotechnology Drugs)

1)
5 ml of 0.9% Saline—given quickly or over a few minutes;
30 ml of Drug #1—given over 60 minutes;
10 ml of Drug #2—given over 20 minutes; and
5 ml of 0.9% Saline—given quickly or over a few minutes.

2)
5 ml of 0.9% Saline—given quickly or over a few minutes;
30 ml of Drug #1—given over 60 minutes;
5 ml of 0.9% Saline—given quickly or over a few minutes;
10 ml of Drug #2—given over 20 minutes; and
5 ml of 0.9% Saline—given quickly or over a few minutes.

3)
5 ml of 0.9% Saline—given quickly or over a few minutes;
60 ml of Drug #1—given over 60 minutes tapered linearly beginning at a rate of 10 ml/hr and ending at a rate of 110 ml/hr.;
15 ml. of Drug #2—given over 30 minutes; and
5 ml of 0.9% Saline—given quickly or over a few minutes.

Another embodiment of a fluid bag 90, in accordance with the invention, is shown in FIGS. 5, 6A, 6B and 6C. In this embodiment, the fluid bag includes a high-pressure clip 92 that is completely closed when the bag is in transport preventing fluid from leaking from the bag or from moving between chambers. The clip includes a first bar 94 having two notched prongs 96, and a second bar 98 having two corresponding sockets 100 for receiving the prongs. The bars may also include alignment holes 107 for specifically aligning the clip in the pump. The clip may be formed of metal or relatively rigid plastic and the two bars may be attached by a small wire or flexible plastic strip 101. The prongs each have a dual position latch 102 which engages a ledge 104 in the socket. After the clip is closed to the second latch position, it closes the passage ways (see FIG. 6C) and cannot be opened with reasonable manual effort. The clip is engaged on the bag over the chamber passageways 108, 110, 112 and 114 through two clip holes 106 in the bag. The clip is automatically released and opened only when the bag is placed in an infusion pump of the invention, and the pump's door is properly closed, the latch is automatically opened by the pump to a first open position (see FIG. 6B).

In this embodiment, the pump also includes a low-pressure clamp. When the bag is properly placed in the pump and the door is properly closed, the low-pressure clamp or pad of the pumping device lays parallel next to the clip and seals off the chamber passageways 108, 110, 112 and 114 at a pad location 115 and simultaneously the clip is opened. The low-pressure clamp generates sufficient pressure to prevent any fluid flow through the chamber passageways until a minimum of pressure is applied to the chambers by the pump. When the pump generates enough pressure within a chamber, the fluid in the chamber is forced underneath and past the clamp through the corresponding chamber passageway to a common passage 116 which leads to the outlet port 118. The bag may also include a pressure sensing dome 120 which is fluidly coupled to the common passage. The pressure sensing dome may be used to provide occlusion detection or pressure control. The pump pressurizes the bag in a linear sequence from the bag's top to its bottom. Again, because each chamber's size and shape governs how the contents of each respective chamber will be administered, the bag may be configured to match the designed drug regimen.

In this embodiment, the bag's chambers can be filled with its base solutions (diluent) through the outlet (and fill) port 108 in the following manner. The high pressure clip 92 is released either by a special filling device which automatically releases the clip as the proper solution(s) are flowing into the bag or by a specially designed hand release device. Additionally, the bag may include filling ports for each chamber (not shown, see e.g., FIG. 1) and fluids or drugs may be added through these filling ports on an opposite side of the bag.

FIGS. 7A–7D show another embodiment of a fluid bag 122 of the present invention. The bag is shown with four chambers 22, 24, 26 and 28 for implementing the SASH infusion procedure. In this embodiment, the bag includes an integral connector 124 for coupling to an infusion tube (not shown). The integral connector allows the bag to be more integrated and simplifies the procedure for inserting the bag into an infusion pump. The bag further includes associated passageways 108, 110, 112 and 114 from each chamber to a common passageway 116 leading to the connector, a high pressure clip 92, five alignment holes 40, and a pressure sensing dome 120. These components function as described in the previous embodiment shown in FIGS. 5 and 6A–6C.

Figure 8:
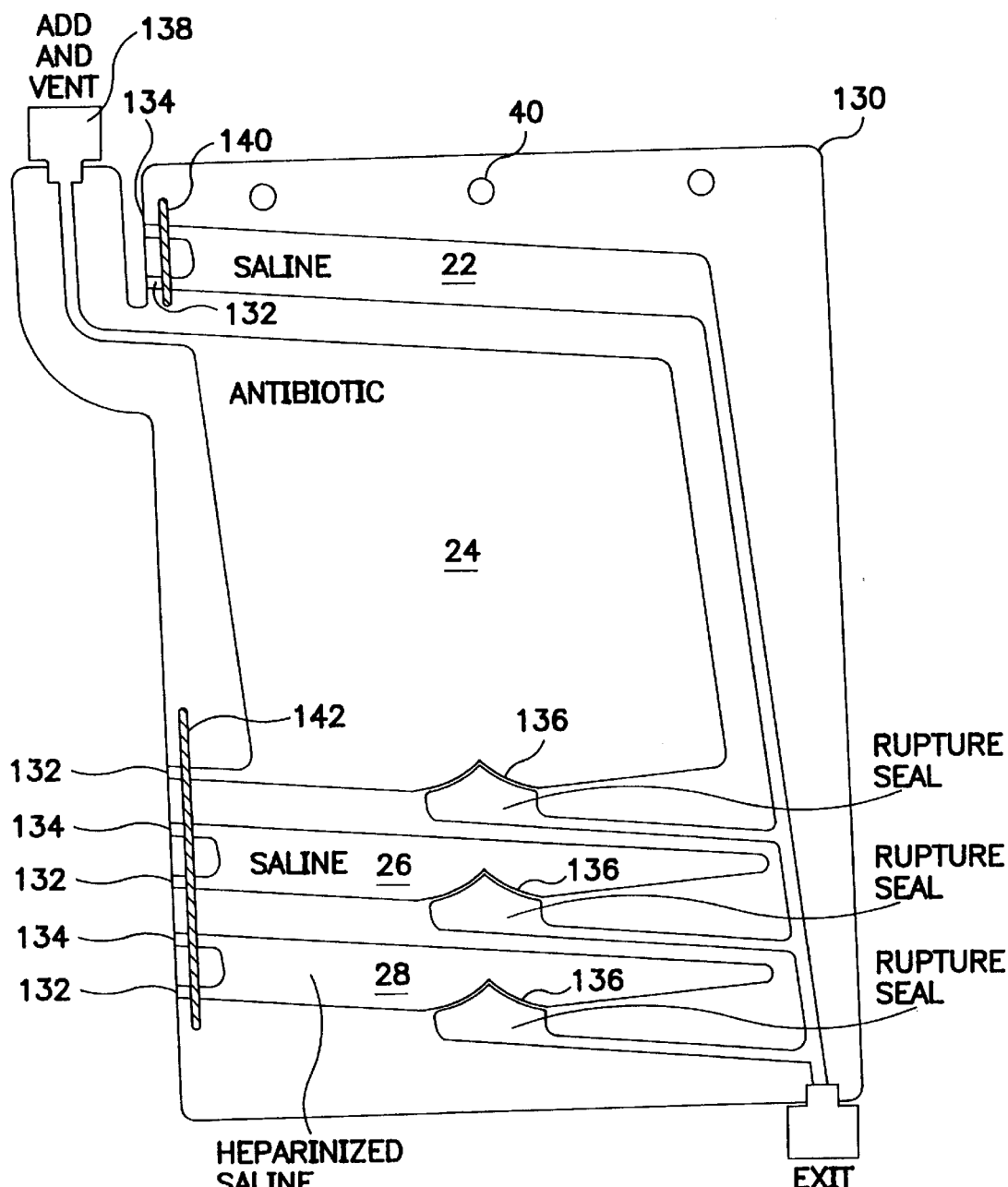
FIG. 8 is an elevation view of a fluid bag, according to the invention, having frangible seals.

FIG. 8 shows another embodiment of a fluid bag of the invention. The bag 130 has features that are similar to the features of the bags discussed above and further includes fill openings 132, vent openings 134 and frangible rupture seals 136. Thus, each of the chambers 22, 24, 26 and 28 has a fill opening 132 and a vent opening 134. The vent part for the drug chamber 24 also includes a resealable or reusable port 138 for adding medication to the chamber.

In this embodiment, the chambers are filled with the prescribed fluids through the fill openings 132. Air is allowed to escape through the vent openings 134 to prevent air bubbles in the chambers. Then all of the openings, except the opening to the additional drug port 138, may be sealed along seal lines 140 and 142 by a heat or ultrasonic seal or the like. An additional seal may seal the drug chamber 24. The seal prevents the addition of additional drugs to the respective sealed chambers. The bag also features frangible rupture seals. As pressure is sequentially applied to the second, third and fourth chambers, respectively, the seal ruptures when the pressure in the corresponding chamber exceeds a predetermined threshold value. Alternatively, the rupture seals may break at incremental increases in the applied chamber pressure such that when increasing pressure is applied to the entire surface of the bag, the rupture seals define the sequence of administration of the fluids in the chambers.

The fluid bag of the invention may be filled by the bag manufacturer or by a pharmacist. The manufacturer may fill the bag's chambers with saline solution, with other base solutions, or with the appropriate medications in a "form, fill and seal" or other manufacturing process. Alternatively, the manufacturer may leave one or more chambers empty. The pharmacist would then complete the prescription using the fill ports. In yet another alternative, medication may be added to a bag through the fill port after the bag is inserted into a pump.

The techniques for applying pressure to the bag may include a linear roller mechanism, a coiled spring mechanism, an air bladder, a series of platens, or other alternative methods. The pressurization technique is chosen in accordance with the designed embodiment of the bag and may be effected by a mechanical, electrical, chemical or other drive means, alone or in combination. Apparatus for implementing representative pressurization techniques are discussed below.

FIGS. 9A and 9B show an embodiment of an infusion pump 150 for expelling the fluids from the chambers 22, 24, 26 and 28 of a fluid bag 152 of the invention. The infusion pump has compartment 154 for receiving the fluid bag. The compartment has a hinged door 156 which is shown in its open position in FIG. 9A. The hinged door includes a release latch 158. At one end of the chamber are a roll-up roller 160 and an opposing roller 162. The roll-up roller travels at a constant speed in conjunction with the opposing roller so that the rollers travel the length of the bag to sequentially compress the bag and sequentially force the fluid from the chambers toward the exit ports. The roll-up roller can be driven by a variety of means, e.g., a spring drive mechanism housed in the enlarged side portion of the pump which also functions as a hand grip. The hand grip is preferably covered with a "soft feel" material. The fluid bag shown in FIG. 9A has three exit ports 164, 166 and 168 that are coupled to an injection molded manifold 170 that functions as fill ports for the chambers and includes check valves. The solutions from the separate chambers are coupled to an exit tube 172.

The infusion pump 150 may have status indicators 174 for indicating the progress of the infusion. The pump may be an entirely mechanical device that may be operated by a spring mechanism. The pump may have a curved back surface 176 for ergonomically fitting again a patient's body.

Figures 10A, 10B:
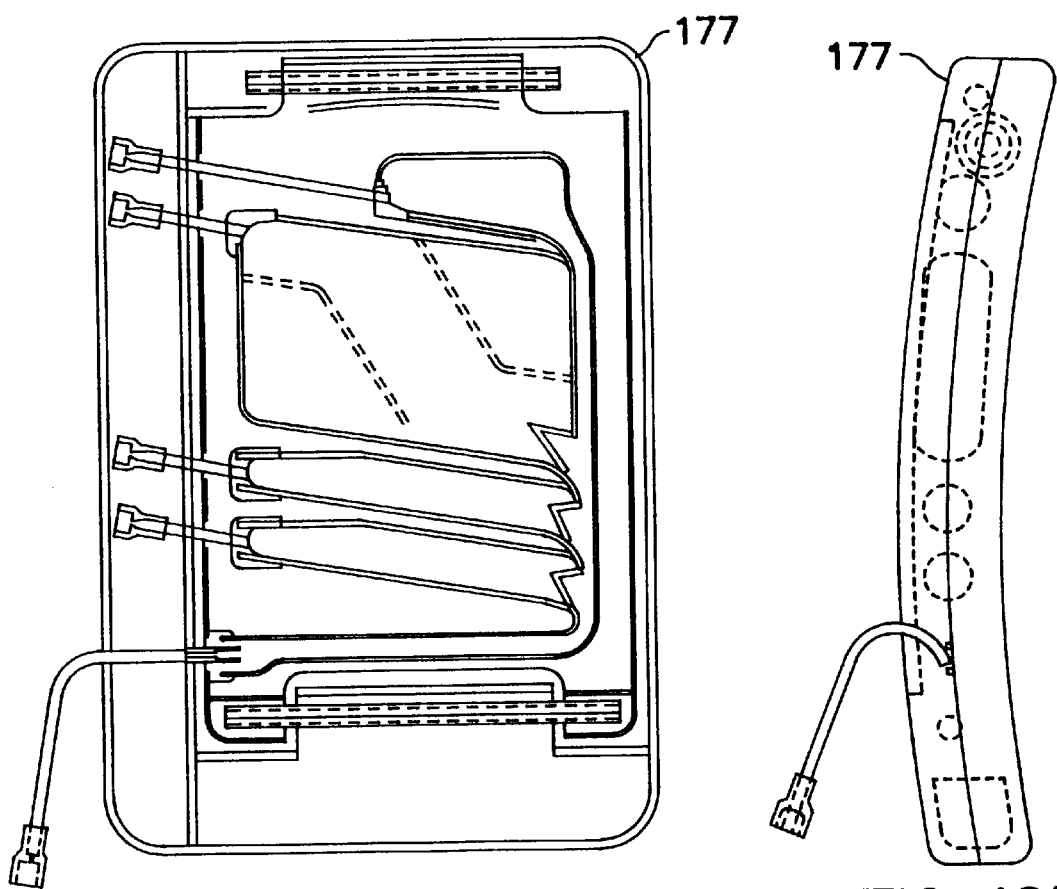
FIGS. 10A–10C are plan and side elevation views, respectively, of the infusion pump of FIGS. 9A and 9B, having an installed infusion bag.
Figure 10C:
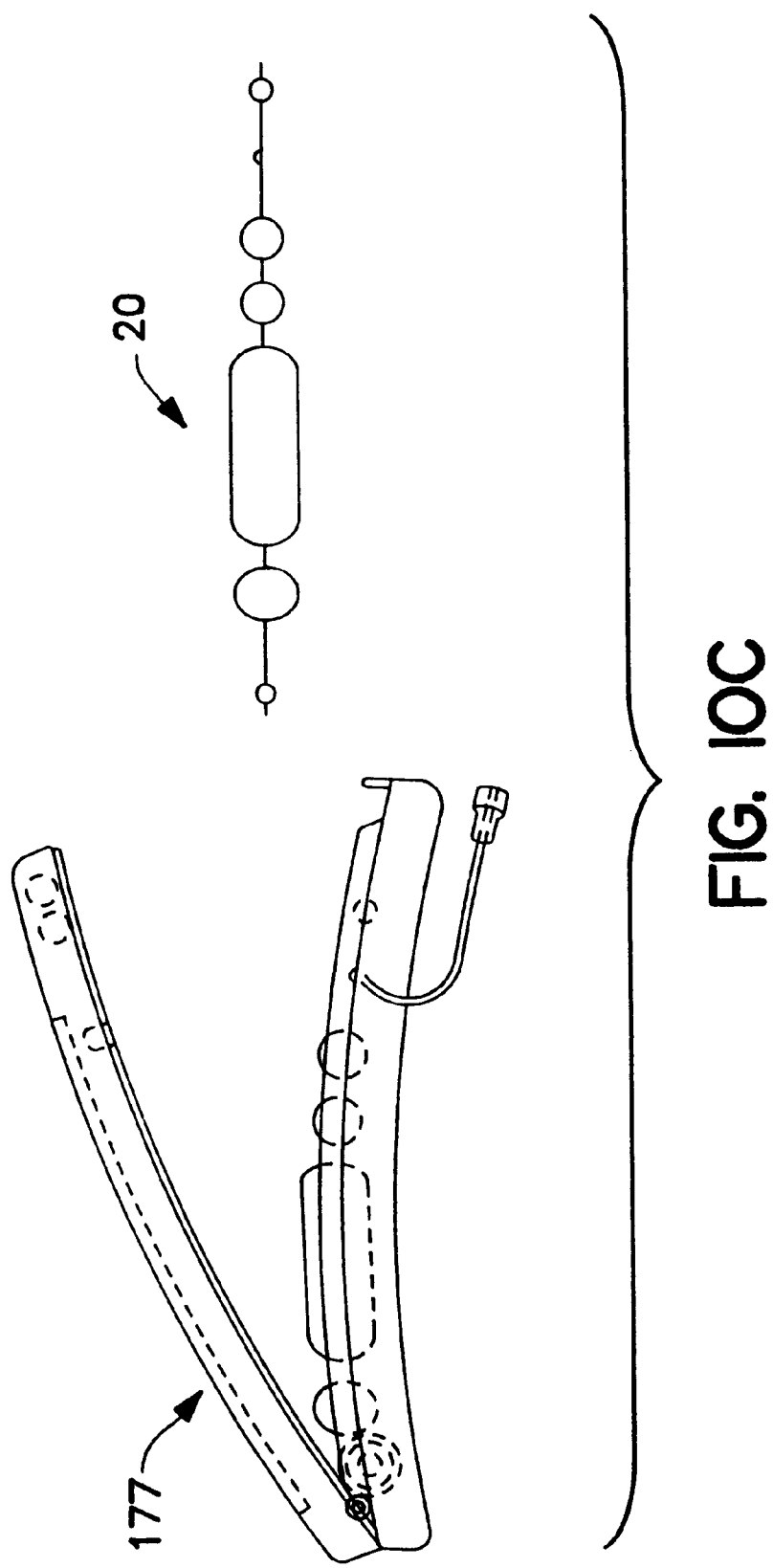

FIGS. 10A–10C show another infusion pump 177 having an installed fluid bag for the administering the SASH infusion procedure. This embodiment of the pump includes electronic control circuits and mechanisms for programmable control of the roller mechanism. Programmable control allows the roller mechanism to operate at a variable rate. Further, the roller mechanism may be stopped between chambers for a desired time interval.

Figure 11A:
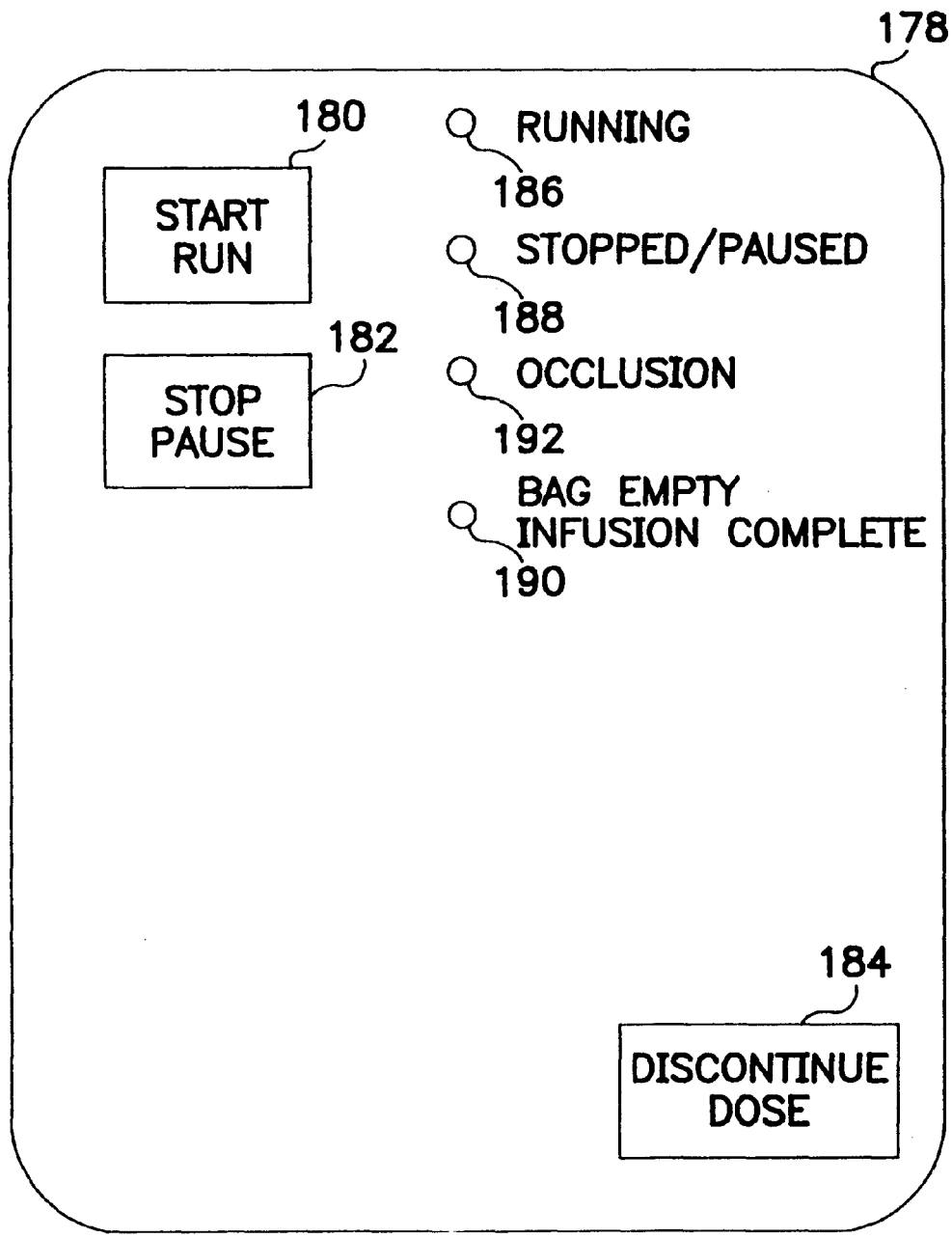
FIGS. 11A and 11B are schematic diagrams showing control panel layouts for two embodiments of the infusion pump of FIGS. 9A and 9B.

FIG. 11A shows a control panel 178 for one embodiment of the infusion pump 177 of FIGS. 10A–10B. The pump's control panel has three buttons and four lights. The first button 180 is a start or run button for beginning the infusion procedure. The next button 182 is a stop or pause button to interrupt the infusion for a relatively brief pause. The third button 184 is a discontinue dose button for terminating the infusion. The lights indicate the status of an infusion and may be light emitting diodes, incandescent lamps, or the like. After the start or run button has been pressed and the roller is sequentially compressing the bag's compartments, the running light 186 will be lit. If the pause button is pressed during the infusion procedure, the stopped/pause light 188 will be lit. When the infusion has been completed, the bag empty light 190 will be lit. An additional light 192 indicates whether an occlusion has occurred in the infusion line leading to the patient.

Figure 11B:
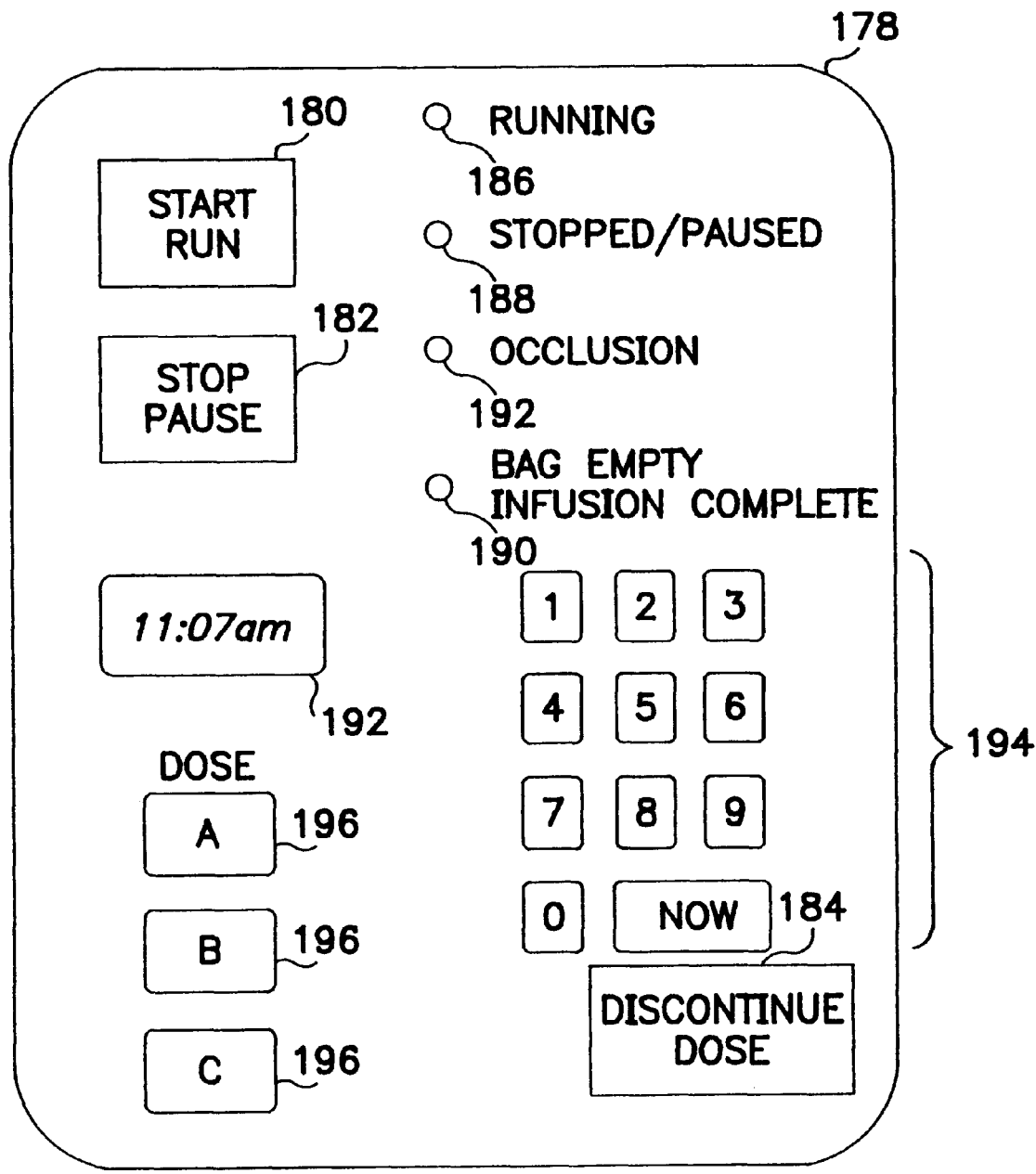

FIG. 11B shows a control panel 178 for a second embodiment of the infusion pump 177 of FIGS. 10A–10C. The panel further includes, in addition to the buttons discussed above with respect to FIG. 10A, a clock 192, a keypad 194, and three dose select buttons 196. The keypad may be used to enter a prescribed infusion therapy. The dosage buttons may be used to select various dose rates or times for a given bag (or times for given chambers within a bag) and corresponding drug therapy.

Figure 12:
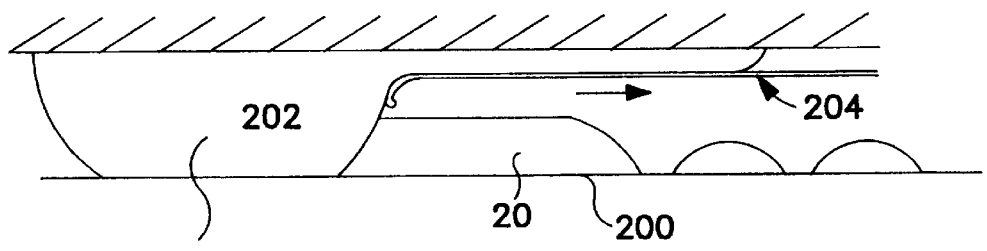
FIG. 12 is a schematic diagram of an inflatable bladder, according to the invention, having an inflation control belt for use in an infusion pump to sequentially empty a fluid bag.

Another embodiment of the infusion pump mechanism for applying pressure sequentially across a bag 20 of the invention is shown in FIG. 12. The bag rests on a relatively rigid surface 200. A pressurized bladder 202 is separated from the bag by a movable belt 204. The bladder is sequentially released by the belt thus applying sequential pressure across the bag. The belt accordingly replaces, for example, the function of the roller in the infusion pump of FIGS. 9A and 9B. The speed at which the belt releases the bladder controls the pumping speed of the infusion pump.

Figure 13:
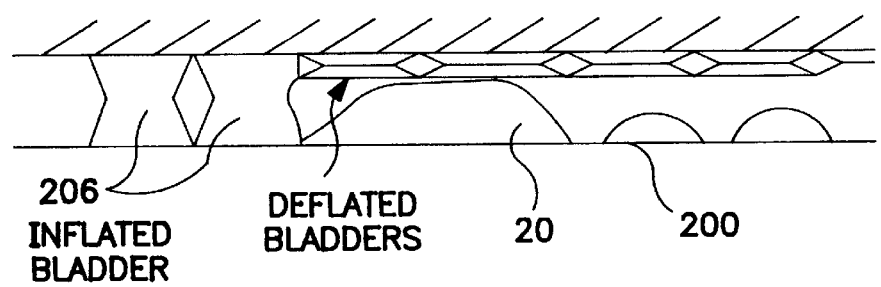
FIG. 13 is a schematic diagram of a plurality of inflatable bladders, according to the invention, for use in an infusion pump to sequentially empty a fluid bag.

Yet another embodiment of the infusion pump pressure mechanism is shown in FIG. 13. Pressure is applied to the bag 20 by a series of inflatable bladders 206. The bladders are inflated sequentially so that the series of bladders perform the same function as the rollers shown in FIGS. 9A and 9B. A timer or a pressure sensor feedback mechanism (not shown) initiates the inflation of each subsequent bladder of the series of the desired time.

Figure 14:
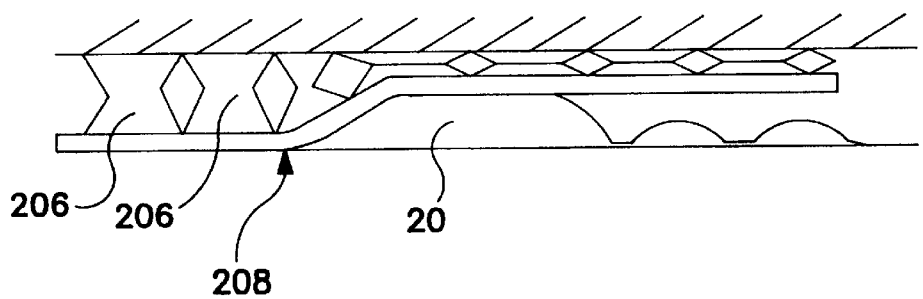
FIG. 14 is a schematic diagram of a plurality of inflatable bladders, according to the invention, that act against a flexible pad for use in an infusion pump to sequentially empty a fluid bag.

Another embodiment of the infusion pump pressure mechanism is shown in FIG. 14. The mechanism includes a series of bladders 206 that press a flexible pad 208 against the bag. The bladders are inflated sequentially and the flexible pad operates to smooth out pressure variations caused by the inflation of each individual bladder.

Figure 15:
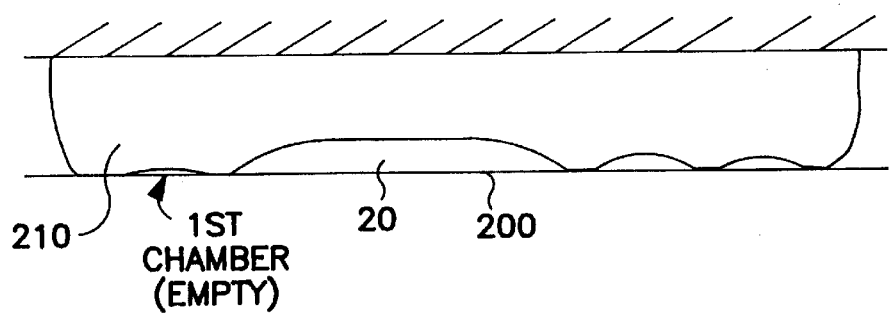
FIG. 15 is a schematic diagram of an inflated bladder, according to the invention, for use in an infusion pump having active valves for controlling the fluid flow from each chamber to sequentially empty a fluid bag.

An additional embodiment the infusion pump, shown in FIG. 15, has a single bladder 210 that is pressurized after the bag is installed in the pump. The pump further includes valves configured to press against the respective passages of the chambers. The flow rate and sequence of fluids flowing from the chambers may be controlled by the valves, the applied pressure, and restrictive orifices to actively control the infusion process.

While the foregoing has been with reference to specific embodiments of the invention, it will be appreciated by those skilled in the art that these are illustrations only and that changes in these embodiments can be made without departing from the principles of the invention, the scope of which is defined by the appended claims.

What is claimed is:

1. A fluid delivery apparatus for the automated sequential or concurrent infusion of a plurality of pharmacological agents, said apparatus comprising a plurality of chambers each configured with a respective geometry, wherein each chamber configuration controls the volume of each pharmacological agent administered, the rate at which each pharmacological agent is administered, and the regimen with which said pharmacological agent is administered.

2. A fluid delivery apparatus as defined in claim 1, further comprising:
a common passageway; and
a plurality of chamber passageways, each chamber passageway being coupled between the common passageway and a respective chamber.

3. A fluid delivery apparatus as defined in claim 2, further comprising a high pressure clip having at least first and second positions, wherein, in the first position, the clip closes the plurality of chamber passageways, and in the second position, the clip permits fluid flow through the plurality of chamber passageways.

4. A fluid delivery apparatus as defined in claim 3, wherein the high pressure clip comprises first and second bars, the first bar has two double notched prongs and the second bar has two sockets, each socket having a ledge for engaging a respective notched prong.

5. A fluid delivery apparatus as defined in claim 4, wherein the first and second bars are coupled by a small flexible plastic strip.

6. A fluid delivery apparatus as defined in claim 2, further comprising a pressure sensing dome in fluid communication with the common passageway.

7. A fluid delivery apparatus as defined in claim 2, wherein the common passageway is coupled to an outlet port.

8. A fluid delivery apparatus as defined in claim 2, wherein the common passageway is coupled to an integral connector.

9. A fluid delivery apparatus as defined in claim 2, further comprising a frangible rupture seal between at least one chamber and the corresponding chamber passageway.

10. A fluid delivery apparatus as defined in claim 1, wherein at least one chamber includes a sealable fill port and a sealable vent port.

11. A fluid delivery apparatus as defined in claim 1, wherein at least one chamber includes a resealable port.

12. A fluid delivery apparatus as defined in claim 1, further comprising an infusion pump with a spring driven roller for sequentially compressing the plurality of chambers.

13. A fluid delivery apparatus as defined in claim 12, wherein the pump includes hinged door having a release tab.

14. A fluid delivery apparatus as defined in claim 1, further comprising an infusion pump actuated by an electrically driven motor for applying pressure to the chambers.

15. A fluid delivery apparatus as defined in claim 14, wherein the pump includes a display having status indicator lights, dose buttons, control buttons, a keypad, and a clock for controlling and indicating the status of an agent administration.

16. A fluid delivery apparatus as defined in claim 1, further comprising an infusion pump having an inflatable bladder for applying pressure to the chambers.

17. A fluid delivery apparatus as defined in claim 16, wherein the pump includes a belt for sequentially releasing the bladder for applying pressure to the chambers.

18. A fluid delivery apparatus as defined in claim 16, wherein the pump bladder includes a series of sequentially inflatable bladders for sequentially applying pressure to the chambers.

19. A fluid delivery apparatus as defined in claim 18, further comprising a flexible bladder pad coupled to the series of bladders for transferring pressure from the series of bladders to the chambers and locally distributing the force applied by any one of the series of bladders.

20. A fluid delivery apparatus as defined in claim 16, further comprising valves that are controllably opened to determine the sequence by which the agents are administered.

21. A fluid delivery apparatus as defined in claim 1, wherein the chambers are configured to sequentially administer the agents.

22. A fluid delivery apparatus as defined in claim 1, wherein the chambers are configured to concurrently administer at least two of the agents.

23. A fluid delivery apparatus as defined in claim 1, wherein the, wherein each chamber's size and shape controls the rate, volume, and time the agents are administered.

24. A fluid delivery apparatus as defined in claim 1 wherein each chamber's position controls time the agents are administered.

25. An automated fluid delivery apparatus for sequentially or concurrently infusing a plurality of medications, comprising a fluid bag which is constructed from medical grade plastic sheets that are bonded together in a manner to define a plurality of separate chambers lying in a plane, each chamber being configured with a respective geometry position and sequence for controlling the rate, volume and time of medication administration.

26. An automated fluid delivery apparatus as defined in claim 25, wherein the rate of fluid flow from the chambers is controlled by an orifice.

* * * * *